United States Patent [19]
Denti et al.

[11] 4,306,972
[45] Dec. 22, 1981

[54] DIALYSIS APPARATUS

[75] Inventors: Ennio Denti, Pino Torinese; Giuseppe T. A. Freda, Asti; Renzo Gervasio, Turin; Sergio Graglia, Torrazza Piemonte, all of Italy

[73] Assignee: Sorin Biomedica S.p.A., Saluggia, Italy

[21] Appl. No.: 197,433

[22] Filed: Oct. 16, 1980

[30] Foreign Application Priority Data

Nov. 23, 1979 [IT] Italy .................................. 69268 A/79

[51] Int. Cl.$^3$ ............................................ B01D 31/00
[52] U.S. Cl. .................................. 210/321.3; 210/450
[58] Field of Search .................... 210/450, 456, 321.1, 210/321.2, 321.3

[56] References Cited
U.S. PATENT DOCUMENTS 4,141,835  2/1979  Schael et al. .................. 210/456 X
4,219,426  8/1980  Spekle et al. .................. 210/456 X Primary Examiner—Frank A. Spear, Jr.
Attorney, Agent, or Firm—Sughrue, Mion, Zinn, Macpeak and Seas

[57] ABSTRACT

Dialysis apparatus is provided of the type comprising a casing housing a central cylindrical core which is surrounded by a plurality of layers of capillary tubes constituted by hollow, semi-permeable, fibres. Blood to be treated is caused to flow through the capillary tubes while dialysing solution is passed over the outer surfaces of the tubes. To facilitate the construction of dialysis apparatus with different dialysing surface areas without altering the dimensions of the casing or core, the core is arranged to dismountably carry a plurality of spacing annuli around which the layers of capillary tubes are wound. The diameter of the annuli determines how many layers of capillary tubes can be accommodated in the casing.

5 Claims, 4 Drawing Figures

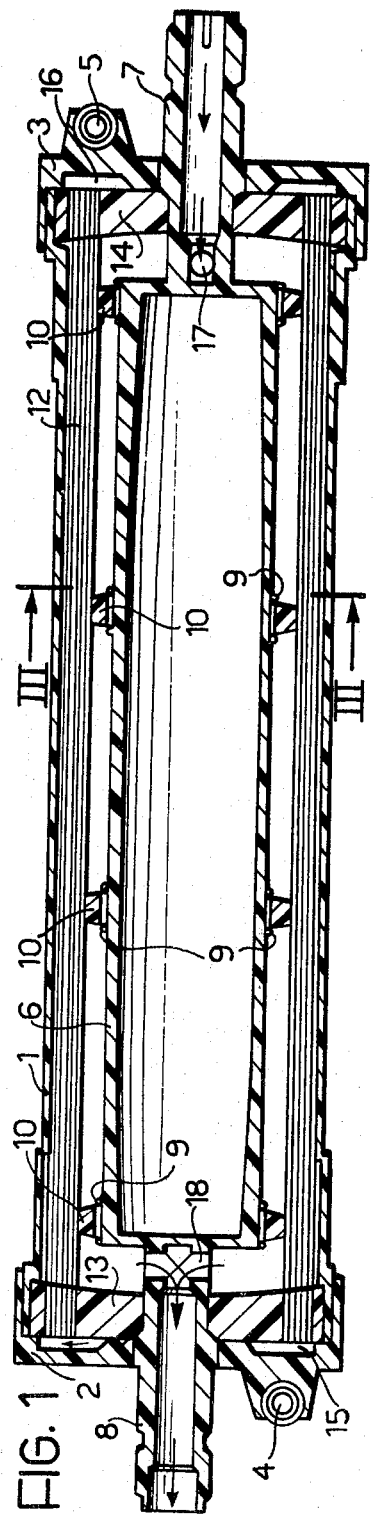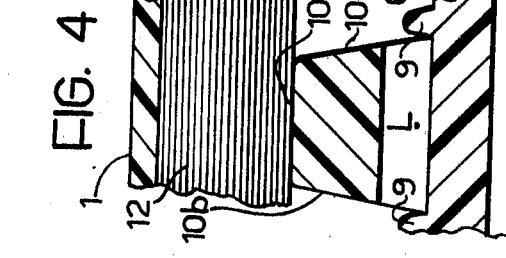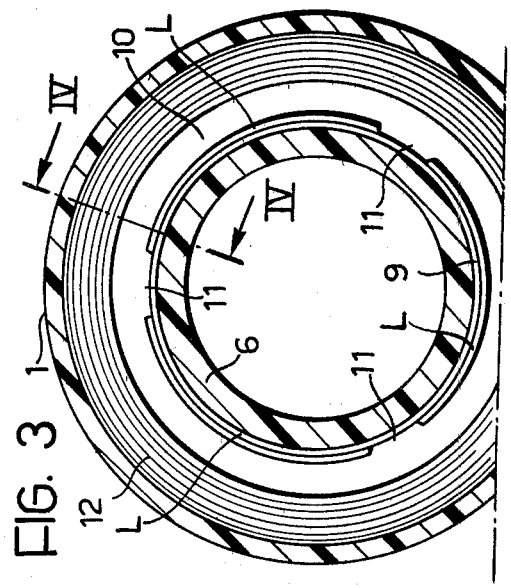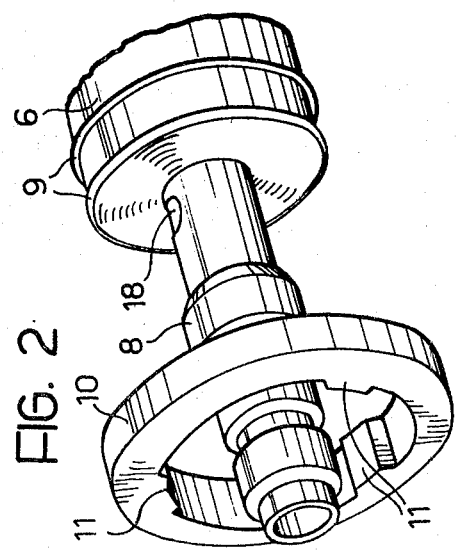

DIALYSIS APPARATUS

The present invention relates to dialysis apparatus.

More particularly, the invention relates to dialysis apparatus of the type comprising an outer casing provided with two end caps respectively formed with a blood inlet and a blood outlet, a central cylindrical core located within said casing and defining an annular space therewith, said core having two end connectors which are externally accessible and serve for the inlet and the outlet respectively of a dialysis solution, a plurality of layers of capillary tubes encompassing said core within said annular space and consisting of semi-permeable hollow fibres, first flow-constraining means arranged to cause blood to pass through the said capillary tubes in its travel between the said blood inlet and outlet, and second flow-constraining means arranged to cause the dialysis solution to pass through said annular space along the outer surfaces of the capillary tubes in its travel between the said inlet and outlet connectors.

Renal dialysis apparatus of the type specified above is known, for example, from German Patent Application No. 2733280, published before examination.

It has been found in practice that the effective dialysing surface area of dialysis apparatus should have a value dependent on the characteristics of the patient under treatment; this requirement has necessitated the manufacture of a range of dialysis apparatus which differ from one another in the quantity of dialysing fibre contained therein. According to known practice, this result is achieved by varying the dimensions of the central core or of the casing; such an approach results in high production costs due particularly to the need to provide several moulds for the manufacture of these components in the various dimensions required. An object of the present invention is therefore to provide dialysis apparatus which lends itself to being made economically with a range of different dialysing surface areas.

This object is achieved in accordance with the present invention by the provision of dialysis apparatus of the type specified above, wherein the outer surface of the said central cylindrical core dismountably carries a plurality of spacing annuli axially spaced from each other, the cylindrical peripheral surfaces of said spacing annuli serving to support the radially inner layer of the said capillary tubes.

By simply varying the dimensions of the spacing annuli the quantity of dialysing fibre contained in the apparatus, and thus the effective dialysing surface area, can be readily changed without alteration to the dimensions of the casing or core.

Preferably, each spacing annulus is retained axially between a pair of annular ribs formed on the central cylindrical core. The shape and dimensions of these ribs are such as to allow the mounting and dismounting of the spacing annuli.

Advantageously each spacing annulus has a trapezoidal shape in cross section so as to facilitate the discharge of the dialysis solution from the dialysis apparatus when the latter is held in a vertical position; this arrangement enables the dialysis apparatus to be effectively washed with dialysis solution and then completely drained.

Preferably each spacing annulus is so formed as to leave a space between its inner surface and the outer surface of the core. Due to this arrangement, during use of the dialysis apparatus, a good flow of dialysis solution is achieved over the radially innermost layer of the capillary tubes, which allows the performance of the dialysis apparatus to be improved compared with known apparatus in which the said innermost layer of capillary tubes is directly in contact with the outer cylindrical surface of the core.

Dialysis apparatus embodying the invention will now be particularly described, by way of example, with reference to the accompanying diagrammatic drawing, in which:

FIG. 1 is an axial, longitudinal section of the dialysis apparatus;

FIG. 2 shows, in perspective, a detail of the FIG. 1 apparatus;

FIG. 3 is a cross section on line III—III of FIG. 1 to an enlarged scale; and

FIG. 4 is a section on line IV—IV of FIG. 3 to an enlarged scale.

The dialysis apparatus shown in the drawing comprises an outer casing 1 provided with two end caps 2 and 3 respectively. The cap 2 is provided with a tangential blood inlet 4 and the cap 3 is provided with a tangential blood outlet 5.

A central hollow core 6 is disposed within the casing 1 and defines jointly therewith an annular space. The two ends of the core 6 are each provided with an axial connector 7, 8 which projects through the corresponding casing end cap 3, 2 and respectively serves for the inlet and for the outlet of dialysis solution.

The outer cylindrical surface of the central core 6 is provided with pairs of annular ribs 9 integrally moulded with the core from a plastics material.

Between each pair of ribs 9 the core 6 dismountably carries a spacing annulus 10. Each annulus 10 has a cylindrical outer surface 10a and two inclined side faces 10b which give the annulus a substantially trapezoidal shape in cross section.

The inner cylindrical surface of each annulus 10 is provided with three radial projections 11, the radial height of which is greater than that of the annular ribs 9 of the core 6. The radially inner surfaces of the three radial projections 11 of each annulus lie on a notional cylindrical surface which has a radius slightly greater than the radius of the outer surface of the cylindrical core 6. Due to this arrangement three spaces L, each in the form of a segment of an annulus, are defined between each spacing annulus 10 and the core 6; furthermore, each annulus 10 when mounted on the core 6 posseses a small amount of radial play which is limited by the three projections 11. The spacing annuli 10 are made of a plastics material and their projections are resiliently deformable to permit the annuli to be removably located between the ribs 9.

Surrounding the core 6 and spaced therefrom by the spacing annuli 10, is a plurality of layers 12 of capillary tubes consisting of hollow semi-permeable fibres. These layers 12 are preferably formed by helically winding around the spacing annuli 10 a strip composed of capillary tubes which are joined together and interwoven.

The end portions of the capillary tubes 12 are set, in known manner, in two annular mounts 13, 14 which seal the spaces between the capillary tubes. These mounts 13, 14 are made of a plastics material and are positioned between the cylindrical inner walls of the casing end portions and the axial connectors 7, 8 whereby to define jointly with the casing end caps 2, 3 two annular chambers 15, 16 respectively in communication with blood inlet 4 and the blood outlet 5.

Blood fed through the inlet 4 of the cap 2 will thus enter the chamber 15 which serves to distribute the blood into the capillary tubes 12. Blood passing out of the tubes at the opposite end of the core 6, enters the chamber 16 which serves to collect the blood and feed it to the outlet 5. The structure defining the chamber 15 and 16 can thus be seen to constitute flow-restraining means in that it constrains blood entering the inlet 4 to pass through the tubes 12 in its travel to the outlet 5.

The base portion of each connector 7, 8 is formed with radial bores 17, 18 which serve to communicate the main axial passage of the connector with the annular space defined between the core 6 and casing 1. Dialysis solution fed into the axial connector 7 passes radially out of the bores 17, along the outer surfaces of the capillary tubes 12, and into the outlet connector 8 through the radial bores 18. The structure defining the radial bores 17, 18 can be seen to constitute further flow-constraining means which serve to constrain the dialysis solution to pass along the outer surfaces of the tubes 12 between the connectors 7, 8.

A portion of the dialysis solution flowing between the connectors 7, 8, will pass over the radially innermost surface of the layers of capillary tubes due to the presence of the spaces L between the inner surface of each annulus 10 and the outer surface of the core 6. As a result the innermost surface of the layers of tubes 12 will effectively contribute to the dialysing surface area of the apparatus. The dimensions of the spaces L are such as not to form a preferential path for the dialysis solution to the detriment of flow past the tubes 12 in the outer layers.

From the preceding description it is clear that by substituting spacing annuli of a greater diameter for the annuli 10 illustrated in the drawing, then without changing the dimensions of the casing 1 or core 6, dialysis apparatus can be made which would possess a smaller dialysing surface area simply due to the fact that less dialysing fibre could be accommodated between the annuli and the casing 1. Similarly, by using spacing annuli of a smaller external diameter or simply by removing these annuli, it is possible to make dialysis apparatus with a greater dialysing surface area than that of the apparatus illustrated.

I claim:

1. In dialysis apparatus comprising an outer casing provided with two end caps respectively formed with a blood inlet and a blood outlet, a central cylindrical core located within said casing and defining an annular space therewith, said core having two end connectors which are externally accessible and respectively serve for the inlet and the outlet of a dialysis solution, a plurality of layers of capillary tubes encompassing said core within said annular space and consisting of semi-permeable hollow fibres, first flow-constraining structure arranged to cause blood to pass through the said capillary tubes in its travel between the said blood inlet and outlet, and second flow-constraining structure arranged to cause the dialysis solution to pass through said annular space along the outer surfaces of the capillary tubes in its travel between the said inlet and outlet connectors, the improvement wherein the outer surface of the said central cylindrical core dismountably carries a plurality of spacing annuli axially spaced from each other, the outer cylindrical peripheral surfaces of said annuli serving to support the radially inner layer of the said capillary tubes while the inner peripheral surfaces of said annuli are each provided with a plurality of radially inwardly extending projections defining therebetween a plurality of restricted passages for the dialysis solution to enable said solution to contact the radially innermost surfaces of said tubes along the length thereof.

2. Dialysis apparatus according to claim 1, wherein the core and the spacing annuli are both made of plastics material with each said annulus being retained axially between a pair of annular ribs formed on said central cylindrical core, the shape and dimensions of said ribs being such as to allow the mounting and dismounting of the annuli.

3. Dialysis apparatus according to claim 2, wherein each said annulus has three equally spaced projections with the radial height of said projections being greater than that of the said annular ribs of the core.

4. Dialysis apparatus according to claim 3, wherein the radially innermost surfaces of the said three radial projections of each annulus lie on a notional cylindrical surface of a radius slightly greater than the radius of the outer surface of the cylindrical core.

5. Dialysis apparatus according to claim 1, wherein each said annulus has a trapezoidal shape in cross section.

* * * * *